United States Patent
Kirsch

[11] Patent Number: 5,443,483
[45] Date of Patent: Aug. 22, 1995

[54] APPLIANCE FOR ACCELERATING THE HEALING OF A BONE SURGERY SITE

[75] Inventor: Axel Kirsch, Postfach 11 68, D70772 Filderstadt, Germany

[73] Assignee: Axel Kirsch, Filderstadt, Germany

[21] Appl. No.: 230,217

[22] Filed: Apr. 20, 1994

[30] Foreign Application Priority Data

Apr. 22, 1993 [DE] Germany ............... 43 13 192.1

[51] Int. Cl.⁶ ..................................... A61F 2/28
[52] U.S. Cl. ..................... 606/74; 600/37; 606/76; 606/151; 606/215; 623/16
[58] Field of Search ............. 600/32, 37; 602/53, 602/58; 604/308; 606/212-216, 105, 203, 74, 151-156; 128/850-856, 887, 888; 623/11, 16

[56] References Cited

U.S. PATENT DOCUMENTS

| | | | |
|---|---|---|---|
| 1,156,440 | 10/1915 | Smith | 606/74 |
| 3,357,432 | 12/1967 | Sparks | 606/151 |
| 3,726,279 | 4/1973 | Barefoot et al. | 606/151 |
| 4,114,624 | 9/1978 | Haverstock | 606/216 |
| 4,127,902 | 12/1978 | Homsy | 623/16 |
| 5,196,016 | 3/1993 | Buser et al. | 606/72 |
| 5,275,602 | 1/1994 | Shimizu et al. | 606/72 |

FOREIGN PATENT DOCUMENTS

615801 7/1935 Germany ............... 606/151

*Primary Examiner*—David Isabella
*Assistant Examiner*—Laura Fossum
*Attorney, Agent, or Firm*—Hill, Steadman & Simpson

[57] ABSTRACT

An appliance for temporarily covering a bone surgery site, such as a recess in a bone filled with bone-building material, such as hydroxylapatite granules, for promoting post-surgery healing includes a flexible sleeve adapted to wrapped around the bone, which carries a covering membrane on one side thereof facing the bone and which carries a reinforcing ply on a side facing away from the bone. The sleeve has two free closure edges, which can be firmly attached to each other with connecting elements which engage into the reinforcing ply, so as to hold the appliance wrapped around the bone.

21 Claims, 4 Drawing Sheets

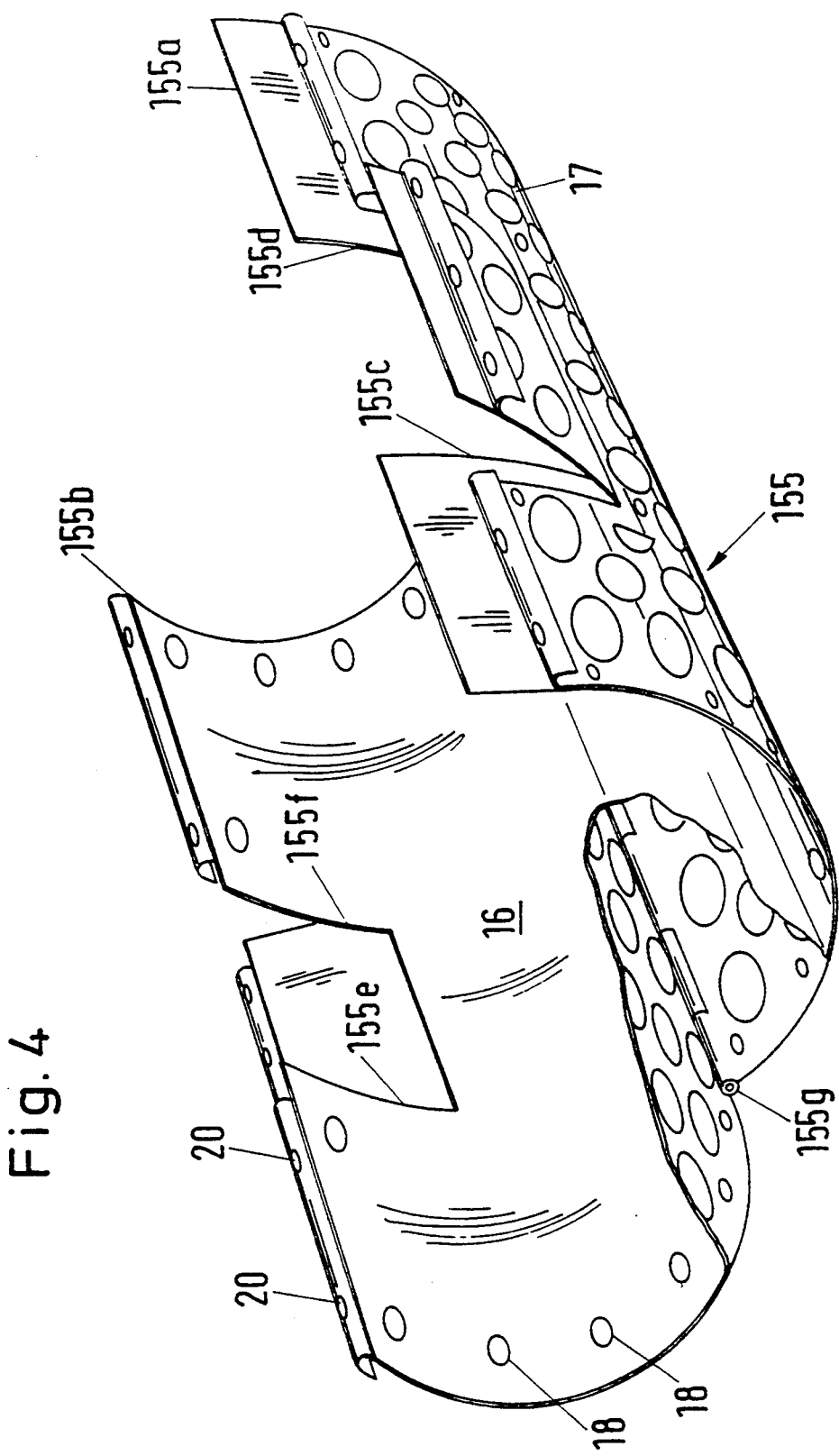

(I)

APPLIANCE FOR ACCELERATING THE HEALING OF A BONE SURGERY SITE

BACKGROUND OF THE INVENTION

1. Field of the Invention

The present invention is directed to an appliance for attachment to a bone at a surgery site for promoting healing of the bone following surgery, and in particular to an appliance for covering a recess in the bone which is filled with bone-forming material such as hydroxylapatite granules with a covering membrane which accelerates healing, with a reinforcing ply for the covering membrane.

2. Related Applications

A post-surgery orthopedic covering is described in co-pending U.S. application Ser. No. 08/188,490 (Kirsch) filed Jan. 28, 1994. The orthopedic covering disclosed therein is for post-surgery treatment of reconstructed bones following plastic surgery or gnathosurgical operations. The covering ensures that the bone-building material will have osseous tissue growing through it essentially only from the side of the covering which faces the bone, but not from the mucous membrane facing the opposite side of the covering, growth from the mucous membrane being undesirable. This ensures that the bone void, recess, flaw or deficiency can be substantially completely eliminated by complete ossification thereof and complete integration of the ingrown osseous tissue with the osseous tissue of the surrounding bone region.

Such a covering membrane, which is preferably composed of absorbable material, is also disclosed in co-pending U.S. application Ser. No. 08/188,584 (Kirsch) filed Jan. 28, 1994, with the addition of a reinforcing ply for seating the covering membrane tightly against the bone on all sides of the surgery site. Such a reinforcing ply can be secured to the bone, for example, by means of fastening pins as disclosed in co-pending U.S. application Ser. No. 08/175,967 (Kirsch et al.) filed Dec. 30, 1993. A disadvantage of the use of such fastening pins, however, is that hammering the pins into the bone normally causes pain to the patient, or requires at least local anaesthesia. A further disadvantage is that the pins must be subsequently removed after the bone has healed, and such removal must be carefully undertaken so that complications do not arise. Such removal may again cause pain, or require local anaesthesia.

SUMMARY OF THE INVENTION

It is an object of the present invention to provide an appliance for holding a covering membrane tightly in place with respect to a bone surgery site for promoting healing of the surgery site, which does not require the use of invasive fastening elements, such as pins, which must traumatically engage the bone.

The above object is achieved in accordance with the principles of the present invention in an appliance of the type described above which has a flexible sleeve that carries the covering membrane at the side of the sleeve facing toward the bone, and which carries the reinforcing ply at a side of the sleeve facing away from the bone, and which has two free closure edges which permit the sleeve to be wrapped around the bone at the surgery site and to be firmly closed in the region of the surgery site by means of connector elements which engage into the reinforcing ply.

The reinforcing ply has, at most, a length extending perpendicularly to the closure edges which corresponds to the smallest circumference of the bone to be covered.

The covering membrane has a length in the direction perpendicular to the closure edges which at least corresponds to the largest circumference of the bone to be covered measured from one closure edge to the other closure edge.

The covering membrane terminates flush with the reinforcing ply perpendicularly to the closure edges along the two ends of the sleeve.

Preferably the edges of the reinforcing ply which proceed parallel to the closure edges are bent away from the bone.

In a preferred embodiment of the invention, the covering membrane projects beyond the reinforcing ply at the side of one closure edge, and terminates along the other closure edge at which the reinforcing ply bends outwardly away from the bone.

In a further embodiment of the invention, the reinforcing ply can be provided with a slot which is formed by a gap in one of the closure edges and which extends perpendicularly to that closure edge circumferentially around a portion of the bone. The slot divides the reinforcing ply into two separated regions.

In a further embodiment of the invention, each of the sleeve, the reinforcing ply and the covering membrane can be provided with such a slot, extending from the closure edge.

In a further embodiment, the two regions of the reinforcing ply which are separated from each other by the slot can be connected flush to each other, while maintaining the two regions of the cover membrane separated, by means of a flap in the reinforcing ply which overlaps the slot.

The covering membrane may project beyond the reinforcing ply along one side of the slot, and may terminate flush with the reinforcing ply along the other side.

In a preferred embodiment of the invention, two such slots are provided at each closure edge, these two slots substantially aligning with each other in the closed condition of the sleeve.

Each slot preferably extends over a maximum of approximately one-fifth of the circumference of the bone.

Fastening elements can be provided to secure the reinforcing ply to the cover membrane. Preferably such fastening elements are rivets which extend through respective bushings in the reinforcing ply and in the covering membrane, the bushings being substantially in registry.

In one embodiment, the rivets may project beyond the covering membrane onto the bone.

As noted above, the closure edges of the sleeve are attached to each other by connecting elements so that the appliance tightly wraps the bone in its closed condition. The connecting elements in the closed condition of the sleeve may pass through bushings in the respective edges of the reinforcing ply which lie opposite each other in the closed condition, the bushings in that closed condition substantially aligning with each other.

The bent edges of the reinforcing ply may have a U-shape, and the bushings can be disposed along the closure edges substantially in the middle of the curve of the U-shaped bend of the reinforcing ply.

The connecting elements can be formed by a thread, such as suture thread, which is non-dissolvable and which has a high tensile strength.

Alternatively, the connecting elements may be pins having respective ends which press firmly against the reinforcing ply at the side thereof facing away from the covering membrane, with these ends of the respective pins being flexible.

The pins may each have such a flexible end and a head disposed at an opposite end. Alternatively, each pin may have two such flexible ends.

The sleeve may be provided with a hinge which is disposed substantially parallel to the closure edges. The hinge may be disposed substantially midway between the bent edges of the reinforcing ply.

Preferably, the closure edges when the sleeve in a closed condition will be oriented on the bone in the proximity of the surgery site, such as a recess filled with bone-building material, so that the bone-building material is tightly surrounded by the covering membrane.

The invention is based on the perception that a bone surgery site can be easily and painlessly firmly surrounded with a covering membrane by employing a sleeve which carries the covering membrane and a reinforcing ply, and the circumference of the sleeve can be matched to the shape of the bone to be treated when connecting the edges of the reinforcing ply by adjusting the distance between these edges. The firm hold provided by the sleeve ensures that no movement of the cover membrane relative to the bone will occur, so that the blood coagulum is converted undisturbed into osseous tissue.

DESCRIPTION OF THE DRAWINGS

FIG. 4 shows a further embodiment of a sleeve constructed in accordance with the principles of the present invention, as viewed obliquely from the front.

DESCRIPTION OF THE PREFERRED EMBODIMENTS

Figure 1:
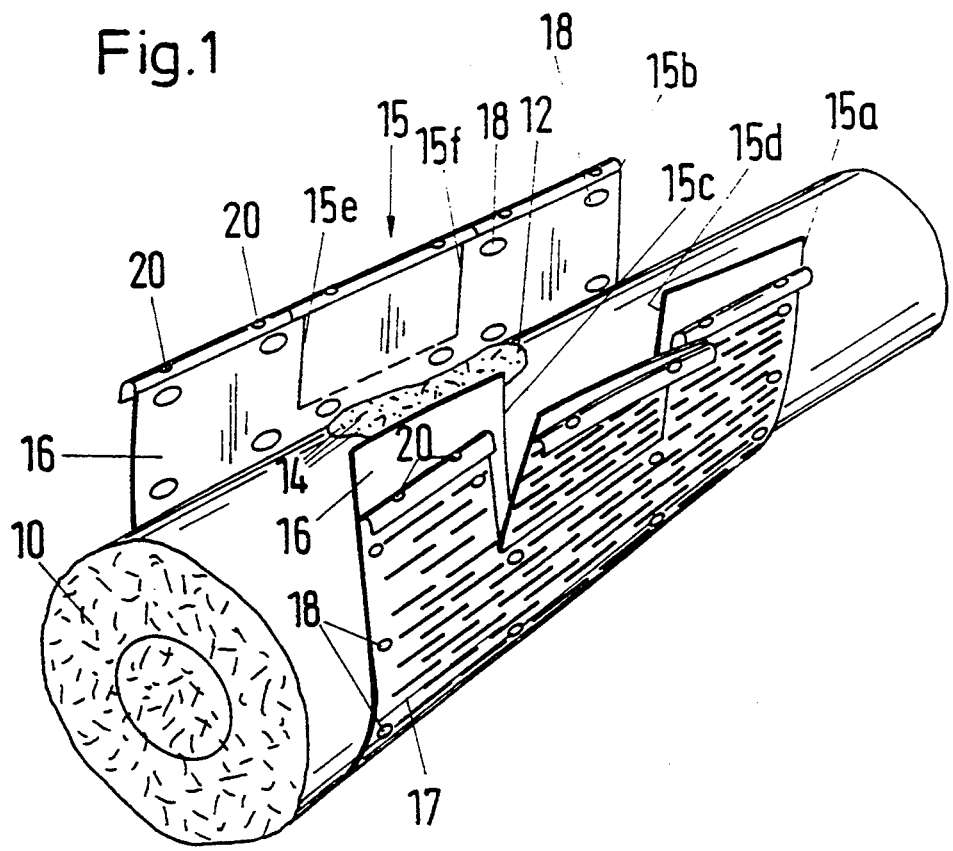
FIG. 1 shows a bone region containing a bone surgery site, in the form of a bone void filled with bone-building material, with an unclosed appliance constructed in accordance with the principles of the present invention, as seen obliquely from the front.

FIG. 1 shows an in vivo bone 10 of a patient, the bone 10 having a void therein in the form of recess 12, the recess 12 being substantially completely filled with bone-building material 14, such as hydroxylapatite granules mixed with bone particles comprised of bone tissue from the patient. Except in the region of the recess 12, the bone 10 is surrounded by an appliance formed by a sleeve 15 with closure edges 15a and 15b which are yet to be joined to each other. The closure edges 15a and 15b are oriented parallel to the longitudinal axis of the bone and are arranged, prior to closure, at a distance from the bone 10 in the proximity of the bone recess 12.

The sleeve 15 has a covering membrane 16 disposed at a side thereof facing toward the bone 10, and has a reinforcing ply 17 arranged at the side of the sleeve 15 facing away from the bone 10.

The edges of the reinforcing ply 17 which lie opposite each other and proceed parallel to the closure edges 15a and 15b are each bent away from the covering membrane 16 in the form of a U-shaped bend.

The covering membrane 16 terminates flush with the reinforcing ply 17 along the two ends of the sleeve 15 proceeding perpendicularly to the closure edges 15a and 15b. The covering membrane 16 projects beyond the closure edge 15a but terminates at the other closure edge 15b along a line at which the reinforcing ply 17 bends outwardly away from the bone 10. Proceeding circumferentially around the bone 10 from one closure edge 15a to the other closure edge 15b, the covering membrane 16 has a length which corresponds to the maximum circumference of the bone 10 to be covered, which enables a tight wrapping of the sleeve 15 around the bone 10.

The sleeve 15 has two slots 15c and 15d extending perpendicularly from the closure edge 15a, and slots 15e and 15f extending perpendicularly from the closure edge 15b. The pair of slots 15c and 15d, extend from the closure edge 15a over approximately one-fifth of the circumference of the sleeve 15 toward the other closure edge 15b, and similarly the pair of slots 15e and 15f extend from the closure edge 15b over approximately one-fifth of the circumference of the sleeve 15 toward the other closure edge 15a. The respective regions of the sleeve adjacent the closure edges 15a and 15b are thus each divided into three sleeve regions.

The regions of the reinforcing ply 17 which are separated from each other by the slots 15c and 15d, and 15e and 15f, can be brought flush against each other by means of a flap formed between each pair of slots, causing corresponding regions of the covering membrane 16 to overlap. This overlap is produced, for example, by the sleeve region between the slots 15c and 15d terminating flush with the reinforcing ply 17 along each of the slots 15c and 15d, but the covering membrane 16 of each of the two outer sleeve regions, on opposite sides of the flap, projects slightly beyond the slots 15c and 15d. Similarly, at the opposite edge of the sleeve 15, the covering membrane 16 of the sleeve region between the slots 15e and 15f terminates flush with the reinforcing ply along the slots 15e and 15f, but the covering membrane 16 at the respective end sleeve regions projects slightly beyond the slots 15e and 15f into the opening formed by the flap. This overlap permits a tight closing of the slots 15c, 15d, 15e and 15f, particularly for a bone having a circumference which changes in size along the longitudinal axis of the bone 10, since the presence of the slots avoids the creation of folds, as described in more detail below.

Figure 2:
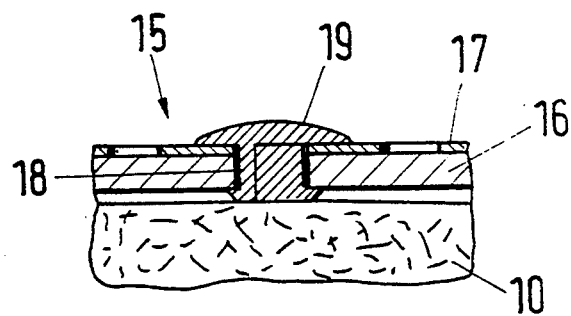
FIG. 2 shows a section through the appliance of FIG. 1 in the region of a fastening rivet.

As can be seen in FIG. 2, the reinforcing ply 17 is secured to the cover membrane 16 by fastening rivets 19. The fastening rivets 19 project through respective bushings 18 in the covering membrane 16 and the reinforcing ply 17 which are in registry, and the fastening rivets 19 project beyond the covering membrane 16 so that they press the sleeve 15 onto the bone 10 in the closed condition of the sleeve, and thus secure the hold of the sleeve 15 on the bone 10 while minimizing friction between the covering membrane 16 and the bone-building material 14.

Figure 3:
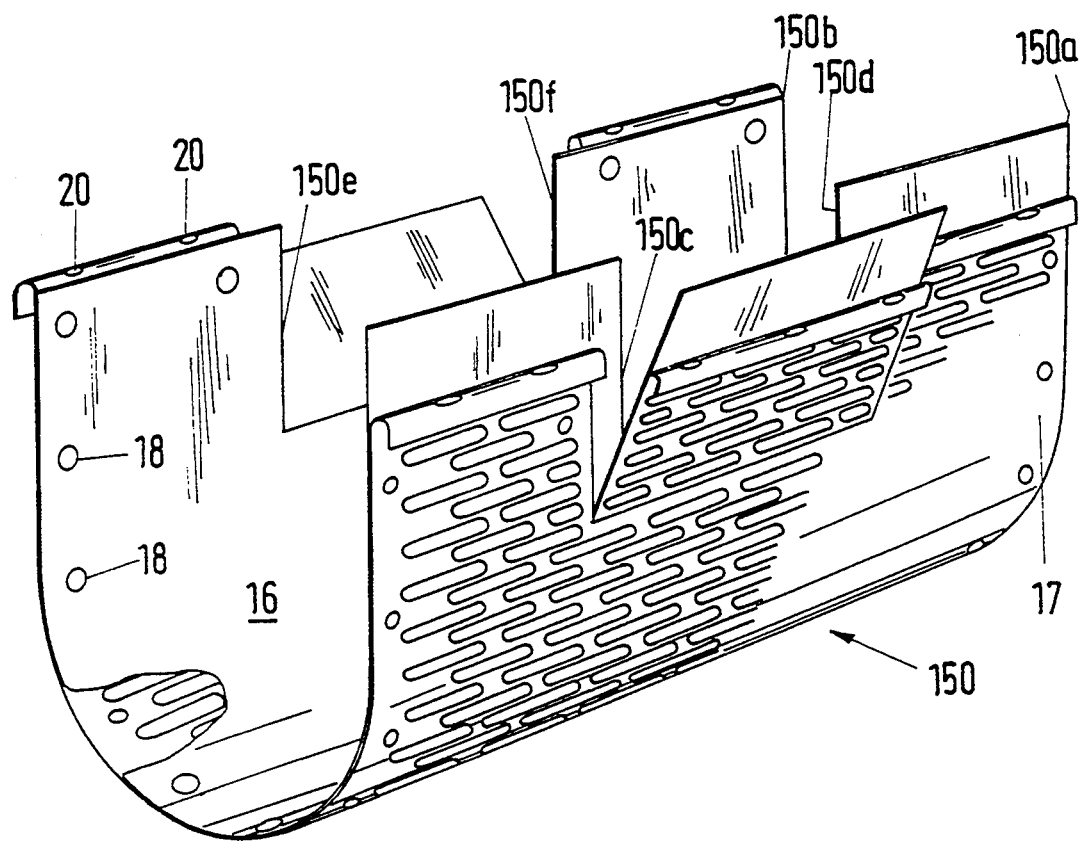
FIG. 3 shows an appliance constructed in accordance with the principles of the present invention, as viewed obliquely from the front.

An embodiment of a sleeve 150, corresponding to the embodiment shown partially wrapping the bone 10 in FIG. 1, is shown by itself in FIG. 3. For covering the bone recess 12, the sleeve 150 of the type shown in FIG. 3 is slipped over the bone 10 from that side of the bone 10 disposed opposite the bone recess 12. A further embodiment of a sleeve 155 is shown in FIG. 4, which can be placed around the bone 10 because it includes a hinge 155g disposed midway between and parallel to the bent edges of the reinforcing ply 17.

Comparable to the elements already described in connection with FIG. 1 for the sleeve 15, the sleeve 150 has closure edges 150 a and 150 b and the sleeve 155 has closure edges 155a and 155b. The sleeve 150 similarly has slots 150 c, 150 d, 150 e and 150 f, and the sleeve 155 has slots 155c, 155d, 155e and 155f.

The unclosed sleeve 15 shown in FIG. 1 is brought to a closed condition as follows, with reference to FIGS. 5a and 5b. First, one closure edge 15a, formed only by covering membrane 16, is pressed against the bone 10, so that the bone recess 12 is covered by the covering membrane 16, and so that no fastening rivets 19 lie on the bone-building material 14.

Figure 5A:
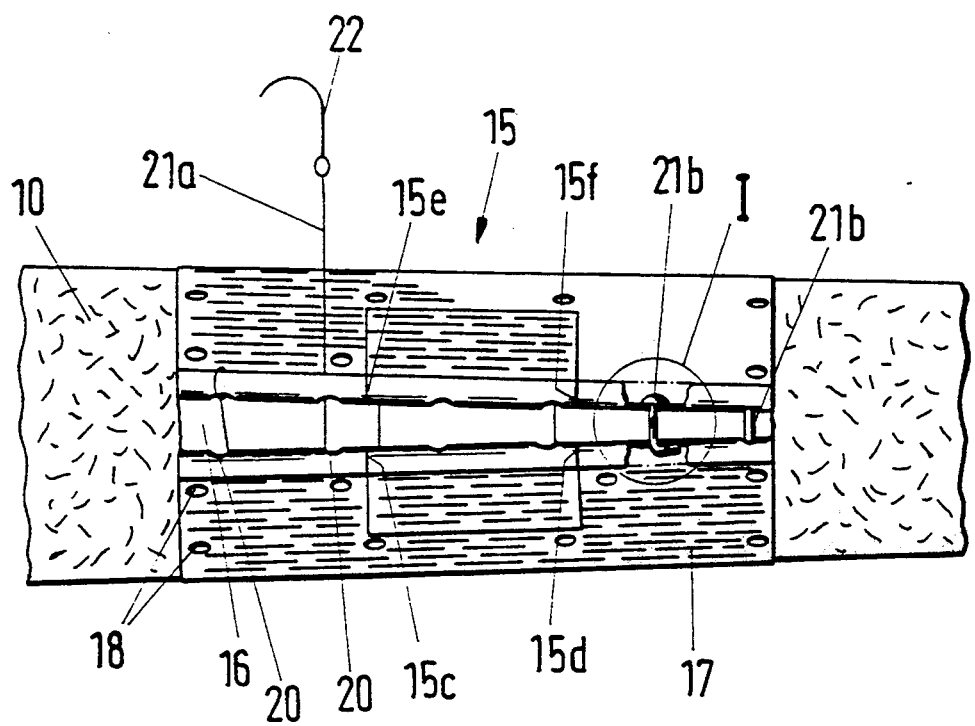
FIG. 5a shows a plan view onto the bone region of FIG. 1 with the appliance closed over the surgery site.
Figure 5B:
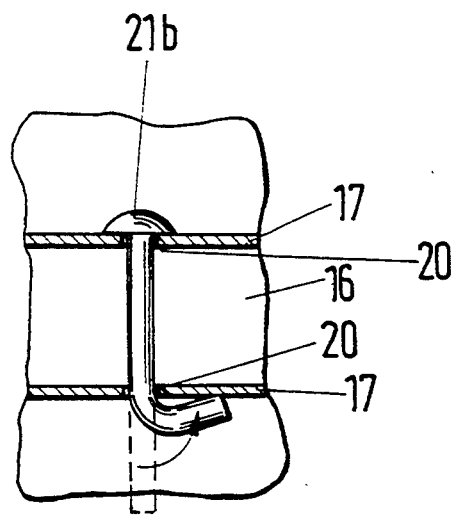
FIG. 5b shows an enlargement of the region I shown in FIG. 5a, with a connecting pin.

The other closure edge 15b of the sleeve 15 is then also pressed against the bone 10, so that the bone recess 12 is covered with at least one layer of covering material 16, and so that the bent edges of the reinforcing ply 17 are not in contact, as can be seen in FIGS. 5a and 5b, since the reinforcing ply 17 has an extent as measured circumferentially around the bone 10 which corresponds to the minimum circumference of the bone 10 to be covered, from one bent edge to the other bent edge.

Next, the bent edges of the reinforcing ply 17 are brought as closely possible to each other, so that, matched to the shape of the bone 10, with the oppositely-disposed regions of the reinforcing ply 17, formed by the slots, having respectively different spacings therebetween. Given a bone 10 as shown in FIG. 5a, which has a changing circumference along its longitudinal axis, i.e., the bone 10 tapers toward the right, the regions of the reinforcing ply 17 disposed at the right edge of the sleeve 15 are disposed closest to each other and the regions at the left-hand edge of the sleeve 15 are at the largest distance from each other. The slots 15c, 15d, 15e and 15f substantially prevent the formation of folds which would otherwise occur due to the distance between the bent edges of the reinforcing ply 17 varying with the varying bone circumference.

The bent edges of the reinforcing ply 17 are provided with bushings 20, which can be seen FIGS. 1, 3 and 4. These bent edges are firmly joined to each other by inserting connecting elements 21a and 21b through bushings 20, which are aligned opposite each other as shown in FIGS. 5a and 5b.

Regions of the sleeve 15 which are separated by larger distances can be held together by sewing with a thread 21a having high tensile strength, which is secured to a hook 22. The hook 22 can be pushed through two bushings 20 disposed opposite each other. The shape and tightness of the sleeve 15 are thereby dependent on the tension of the thread 21a, which is then tied off in a suitable manner.

In the embodiment shown in FIGS. 5a and 5b, the connecting pin 21b has a head at one end, and has an opposite, straight end which is inserted through two of the bushings 20 which are aligned, until the head of the connecting pin 21b comes to lie against the reinforcing ply 17. The straight end of the connecting pin 21b is then bent in order to firmly close the sleeve 15, as shown in FIG. 5b. The shape and tightness of the sleeve 15 are thus also dependent on the locations at which the connecting pins 21b passing through the bushings 20 are bent.

In general, the thread 21a and the connecting pin 21b form length-adjustable connector elements which are firmly connectable to the edges of the reinforcing ply 17. Such length-adjustable connector elements are employed for closing each of the sleeves 15, 150 and 155 of the invention.

Instead of being provided with a head at one end thereof, the connecting pin 21b may be provided with two flexible ends, each of which can be bent in the manner shown in FIG. 5b.

The reinforcing ply 17 and the covering membrane 16 can be held together by any known fastening means, which need not necessarily be in the form of the rivets 19. The fastening means, however, preferably should project beyond the covering membrane 16 at several locations, in order to simultaneously press against the bone 10 and to secure the hold of the sleeve 15, 150 or 155 on the bone 10.

Bones having dimensions which, although similar, are non-uniform along their longitudinal length can be firmly wrapped by a standardized sleeve 15, 150 or 155 in accordance with the invention, because the distance between the bent edges of the reinforcing ply 17, when the sleeve is closed, can be matched to the particular bone shape, whereas it is the dimensioning of the covering membrane 16 which assures that the bone surgery site will be covered by membrane material 16.

As soon as the growth of osseous tissue through the bone-building material 14 has been completed and, assuming the covering membrane 16 consists of absorbable material which has essentially been spent, the sleeve 15, 150 or 155 can be removed from the bone 10 by removing the connecting elements 21a and 21b.

Although modifications and changes may be suggested by those skilled in the art, it is the intention of the inventor to embody within the patent warranted hereon all changes and modifications as reasonably and properly come within the scope of his contribution to the art.

I claim as my invention:

1. An appliance for temporarily covering a surgery site of a bone in vivo comprising:

a flexible sleeve adapted for wrapping around said bone having a covering membrane consisting of material for accelerating healing of said surgical site disposed at a side of said sleeve adapted to face toward said bone, and a reinforcing ply disposed at an opposite side of said sleeve adapted to face away from said bone;

said sleeve having two closure edges proximate each other when said sleeve is wrapped around said bone, said reinforcing ply being exposed along said closure edges;

connecting means, engaging said reinforcing ply along said two closure edges, for connecting said closure edges for firmly holding said sleeve around said bone with said covering membrane covering said surgery site;

said reinforcing ply having exposed edges, extending parallel to said closure edges, said exposed edges being bent away from said bone and forming said closure edges engaged by said connecting means; and said covering membrane projecting beyond said reinforcing ply along one of said closure edges, and terminating the other of said closure edges along a line wherein said reinforcing ply bends away from said bone.

2. An appliance as claimed in claim 1 wherein a portion of said bone to be wrapped by said sleeve has a circumference varying from a smallest circumference to a largest circumference, and wherein said reinforcing ply has a length extending perpendicularly to said closure edges which is at most equal to said smallest circumference.

3. An appliance as claimed in claim 1 wherein a portion of said bone to be wrapped by said sleeve has a circumference which varies from a smallest circumference to a largest circumference, and wherein said covering membrane has a length extending perpendicularly from one of said closure edges to the other of said closure edges which is at least equal to said largest circumference.

4. An appliance as claimed in claim 1 wherein said sleeve has opposite ends extending perpendicularly to said closure edges, and wherein said covering membrane terminates flush with said reinforcing ply at each of said opposite ends of said sleeve.

5. An appliance for temporarily covering a surgery site of a bone in vivo comprising:
a flexible sleeve adapted for wrapping around said bone having a covering membrane consisting of material for accelerating healing of said surgical site disposed at a side of said sleeve adapted to face toward said bone, and a reinforcing ply disposed at an opposite side of said sleeve adapted to face away from said bone;
said sleeve having two closure edges proximate each other when said sleeve is wrapped around said bone, said reinforcing ply being exposed along said closure edges;
connecting means, engaging said reinforcing ply along said two closure edges, for connecting said closure edges for firmly holding said sleeve around said bone with said covering membrane covering said surgery site; and
each of said covering membrane and said reinforcing ply having at least one slot disposed perpendicularly to one of said closure edges, each of said covering membrane slot and said reinforcing membrane slot extending from one of said closure edges and proceeding circumferentially around a portion of said sleeve, said slot in said reinforcing ply dividing said reinforcing ply into separated regions, said separated regions of said reinforcing ply lying flush to each other, said slot in said covering membrane dividing said covering membrane into separated regions, said separated regions of said covering membrane overlapping each other.

6. An appliance as claimed in claim 5 wherein said slot in said reinforcing ply and said slot in said covering membrane are oriented relative to each other so that said slot in said covering membrane projects beyond one side of said slot in said reinforcing ply and terminates flush with an opposite side of said reinforcing ply.

7. An appliance as claimed in claim 5 wherein said slot in said reinforcing ply and said slot in said covering membrane extend to a maximum of approximately one-fifth of a circumference of said sleeve.

8. An appliance as claimed in claim 5 wherein said slot in said reinforcing ply and said slot in said covering membrane extend to a maximum of approximately one-fifth of a circumference of said sleeve.

9. An appliance as claimed in claim 1 wherein said reinforcing ply and said covering membrane each have a pair of slots therein, said pairs of slots respectively extending from said closure edges, and each pair of slots aligning with each other when said sleeve is wrapped around said bone.

10. An appliance as claimed in claim 9 wherein said slots comprising each pair of slots extend to a maximum of approximately one-fifth of a circumference of said sleeve.

11. An appliance for temporarily covering a surgery site of a bone in vivo comprising:
a flexible sleeve adapted for wrapping around said bone having a covering membrane consisting of material for accelerating healing of said surgical site disposed at a side of said sleeve adapted to face toward said bone, and a reinforcing ply disposed at an opposite side of said sleeve adapted to face away from said bone;
said sleeve having two closure edges proximate when said sleeve is wrapped around said bone, said reinforcing ply being along said closure edges;
connecting means, engaging said reinforcing ply along said two closure edges, for connecting said closure edges for firmly holding said sleeve around said bone with said covering membrane covering said surgery site;
each of said reinforcing ply and said covering membrane having a plurality of bushings therein, said bushings in said covering membrane being in registry with said bushings in said reinforcing ply and a plurality of rivets respectively extending through said bushings attaching said reinforcing ply to said covering membrane.

12. An appliance as claimed in claim 11 wherein each of said rivets projects beyond said covering membrane so as to be in contact with said bone when said sleeve is wrapped on said bone.

13. An appliance as claimed in claim 1 wherein said exposed portions of said reinforcing ply at said closure edges have a plurality of bushings therein, said bushings in the exposed portion of said reinforcing ply at one of said closure edges being aligned with the bushings in the exposed portion of the reinforcing ply at the other of said closure edges when said sleeve is wrapped on said bone, and said connecting means extending through said bushings of each of said exposed portions of said reinforcing ply at the respective closure edges.

14. An appliance as claimed in claim 11 wherein each of said exposed portion of said reinforcing ply at the respective closure edges has a U-shaped bend extending away from said bone, each exposed portion of said reinforcing ply having a midline of said U-shaped bend, and said bushings being disposed essentially along said midline.

15. An appliance as claimed in claim 13 wherein said connecting means comprises high-tensile strength thread sewn through said bushings.

16. An appliance as claimed in claim 13 wherein said connecting means comprise a plurality of pins extending through the bushings respectively disposed at said closure edges, each pin having at least one end which is flexible for bending said pin after said pin has been inserted through its bushing to hold said pin in place.

17. An appliance as claimed in claim 16 wherein each of said pins comprises a flexible end and a head disposed at an opposite end.

18. An appliance as claimed in claim 1 wherein said connecting means comprise length-adjustable connecting means.

19. An appliance as claimed in claim 1 wherein said sleeve further comprises a hinge extending substantially parallel to said closure edges.

20. An appliance as claimed in claim 19 wherein said hinge is disposed substantially along a midline between said exposed portions of said reinforcing ply.

21. An appliance as claimed in claim 1 wherein said sleeve is dimensioned so that said closure edges press on said bone adjacent said surgery site so that said covering membrane tightly surrounds said surgery site.

* * * * *